United States Patent [19]

Langrick et al.

[11] Patent Number: 4,856,322
[45] Date of Patent: Aug. 15, 1989

[54] METHOD AND DEVICE FOR MEASURING THE VISCOSITY OF AN INK

[75] Inventors: David J. Langrick, Lubbenham; Mark Smith, Peterborough, both of England

[73] Assignee: Willett International Limited, Slough, United Kingdom

[21] Appl. No.: 224,735

[22] Filed: Jul. 27, 1988

[30] Foreign Application Priority Data

Feb. 17, 1988 [GB] United Kingdom ............... 8803641

[51] Int. Cl.⁴ .......................................... G01N 11/06
[52] U.S. Cl. ...................................................... 73/56
[58] Field of Search ........................................ 73/55, 56

[56] References Cited

U.S. PATENT DOCUMENTS 4,677,845  7/1987  Izumi et al. ............................. 73/56

FOREIGN PATENT DOCUMENTS 1032365  7/1983  U.S.S.R. ............................. 73/55

Primary Examiner—Stewart J. Levy
Assistant Examiner—Joseph W. Roskos
Attorney, Agent, or Firm—Charles D. Gunter, Jr.

[57] ABSTRACT

The invention relates to a method for monitoring the viscosity of ink in a continuous jet ink jet printer, which method comprises causing at least part of the ink to flow through a restricted orifice into a vessel and measuring the time taken to fill the vessel between a lower level limit and an upper level limit and allowing ink to escape from the vessel to reduce the level to below the lower level limit, characterized in that ink is automatically removed from the vessel by a syphon when the ink has reached the upper level limit.

9 Claims, 2 Drawing Sheets

METHOD AND DEVICE FOR MEASURING THE VISCOSITY OF AN INK

The present invention relates to a device, notably to a device for measuring the viscosity of ink flowing in a continuous ink jet printer.

BACKGROUND TO THE INVENTION

In a continuous ink jet printer, ink is ejected continuously through a nozzle as a single jet of ink which is then broken up into a stream of substantially uniformly sized and spaced apart droplets, typically by applying pressure pulses to the ink or by vibrating the nozzle. The droplets are then caused to travel either into a collection gutter or are allowed to fall onto the surface on which the ink is to be applied. Typically, this is done by charging the droplets and then passing them through an electric field. This either causes the charged droplets to depart from their straight line of flight to the gutter so that they miss the gutter and are printed or deflects the droplets into the gutter. The droplets which are collected in the gutter are not printed and are re-cyled to the ink reservoir serving the print head for re-use. However, during their flight and re-cycle, some of the solvent or carrier medium for the ink is lost from the droplets through evaporation.

The proper operation of the print head is dependant, inter alia, upon the viscosity of the ink flowing through the nozzle orifice and this is altered by the loss of solvent or carrier medium from the ink. The viscosity is also affected by the temperature at which the print head is operated and the composition of the ink, both of which latter can vary from print run to print run. It is therefore necessary to ensure that voscosity of the ink is maintained within desired limits at all times and these limits may not be the same for each print run.

In practice this has proved difficult, since the losses of solvent or carrier medium are not consistent and vary considerably with the ambient conditions as well as with the relative proportion of droplets which are recycled to those which are printed. It has been proposed to measure the weight lost from the ink in the reservoir, to allow for that amount lost in being printed and then to add solvent or carrier medium to make up the apparent differences assuming thst this is all lost solvent or carrier medium. However, this is cumbersome and requires that the print head be shut down so that all ink in the system is returned to the reservoir for weighing. Furthermore, it does not take into account any extraneous losses or changes in temperature which can affect the viscosity of the ink.

In another method it has been proposed in Japanese patent application number 21723/1979 to measure the rate of flow of ink using a flow meter in a bypass line in the print head. This requires extensive modification to the ink circuit for the print head. Furthermore, flow meters do not give accurate readings at the comparatively low volume flow rates which are normal in ink jet printers.

It has also been proposed in European Patent Application No. 228828 to measure the time taken for the ink to fill a known volume of a vessel, by measuring the time taken to fill that vessel between a lower and an upper level. In order that such a process can be of any practical use, its operation has to be integrated with the operation of the print head and the solvent make up addition system; and for the process to be operated as often as possible in order to give close monitorng of the condition of the ink. It is therefore proposed that the vessel into which the ink was fed should be emptied by the operation of a valved outlet thereto every time the vessel was filled to the desired upper level. Such a system requires integration of the valve operation with the measurement of the viscosity which requires additional control and computing facilities for the print head. Furthermore, if the valved outlet should become blocked or fail to operate for any reason, back pressure will be generated in the vessel and will feed back into the ink line to the nozzle and affect the operation of the print head.

We have now devised a method for measuring viscosity of ink in a continuous ink jet printer which reduces the above problems in which enables monitoring of the viscosity of the ink to be carried out on a semi-continuous basis.

SUMMARY OF THE INVENTION

Accordingly, the present invention provides a method for monitoring the viscosity of ink in a continuous jet ink jet printer, which method comprises causing at least part of the ink to flow through a restricted orifice into a vessel and measuring the time taken to fill the vessel between a lower level limit and an upper level limit and allowing ink to escape from the vessel to reduce the level to below the lower level limit, characterised in that ink is removed from the vessel by means of a syphon when the ink has reached at least the said upper level limit.

The invention also provides a device for monitoring the viscosity of ink in a continuous ink jet printer which device comprises a vessel having a restricted ink inlet thereto and means for detecting the time taken to fill the vessel between a lower level limit and an upper level limit and an outlet for ink from the vessel, characterised in that the outlet to the vessel is provided with a syphonic means for removing ink from the vessel when ink has reached at least the said upper level limit.

The invention further provides a continuous ink jet printer provided with a device of the invention integrated with means for controlling the addition of make-up solvent or carrier medium to the ink in response to the viscosity monitored by the device of the invention.

The invention further provides a method for operating a continuous ink jet printer wherein make-up solvent or carrier medium is added to the ink in response to monitoring of the viscosity of the ink using a device of the invention.

The invention can be applied to a wide range of types of continuous ink jet printer operating with a wide range of ink types. The device of the invention can be incorporated as original equipment in new printers or can be added as an accessory to existing printers. For convenience, the invention will be described hereinafter in terms of a self-contained unit to be fitted to existing printing machines. However, it will be appreciated that the same principles of operation can be applied to apparatus which is built into new printers, for example incorporated into the structure of the print head itself.

DESCRIPTION OF THE DRAWINGS

The invention will be described with respect to the preferred form thereof as shown in the accompanying drawings in which.

DESCRIPTION OF THE PREFERRED EMBODIMENT

Figure 1:
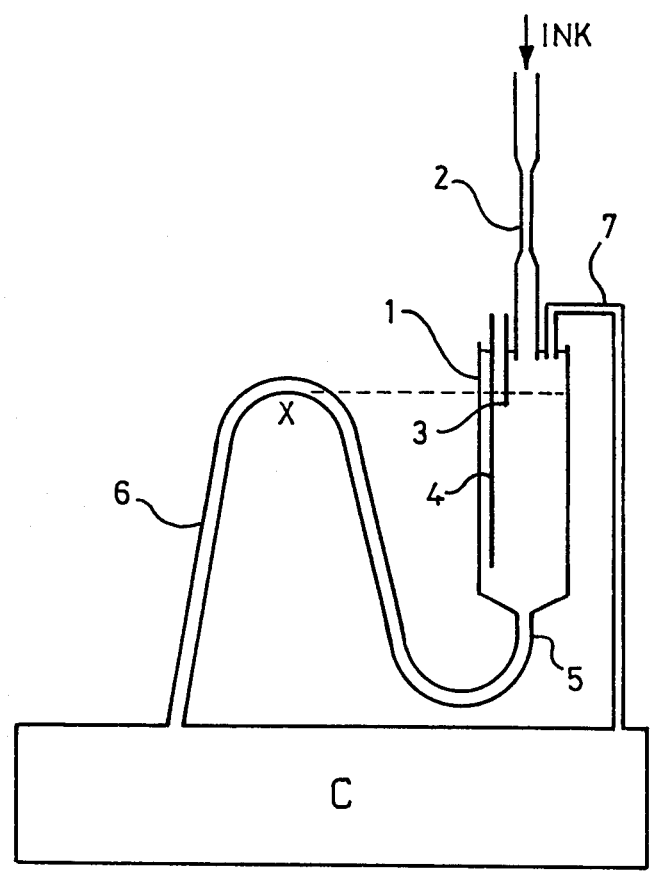
FIG. 1 is a diagrammatic sectional view of the device of the invention and FIG. 2 is a block diagram of a printer incorporating the device of FIG. 1.
Figure 2:
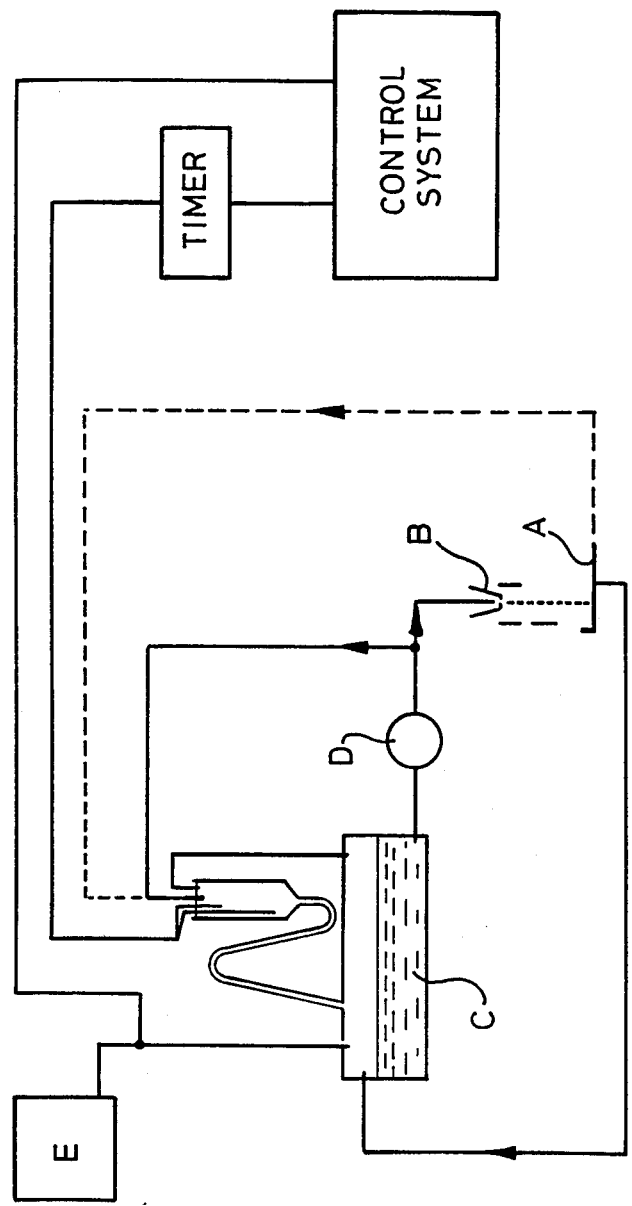

The device of the invention comprises a vessel 1 into which ink from some part of the ink flow circuit of the printer operated at a substantially constant pressure is fed. Typically, as shown in FIG. 2, the printer will comprise an ink reservoir C from which ink is fed under pressure to a print head B by a pump D, the ink droplets caught in the gutter A are returned to the reservoir C. Vessel 1 is preferably fed from ink at the operating pressure of the print head B, for example from the pressure feed line to the print head or from the excess flow return line from the ink pump D, through a restricted inlet 2, typically at a pressure of between 0.5 and 10 bar.

The vessel 1 is provided with means 3 and 4 for sensing when the ink level reaches a lower level and an upper level within the vessel. Any suitable sensor can be used, for example one based on changes in capacitance between the sensor and the wall of the vessel or one triggered by contact with the conductive ink used in the printer. The level sensors are connected to any suitable timing means (not shown) which will detect the time taken to fill the vessel between the lower and upper level sensors. The upper and lower sensors are located at any suitable position within the vessel. However, it is preferred that the lower sensor 4 be located at least 10% of the axial length of the vessel above the outlet to the vessel to provide an adequate buffer time between the end of one operation cycle and the start of the timing of the next filling cycle. It is also preferred that the distance between the lower and upper sensors be such that it will take from 30 to 300 seconds for the vessel to fill between the sensors.

The vessel is also provided with an outlet 5 for returning ink to the circuit of the printer, or discharging it to waste. In the assembly shown the ink is discharged into the ink reservoir C for the printer so that it can be re-used. The outlet 5 can be at any level in the vessel below the level level sensor, but is preferably located at or adjacent the base of the vessel. Outlet 5 feeds a syphon 6, the top level X of which determines the level within the vessel at which emptying of the vessel through the syphon takes place and is located at or above the level of the upper level sensor in vessel 1. Typically, the syphon is a conventional inverted U tube syphon, but other forms of syphon may be used if desired. The vessel 1 and its syphon 6 are located above the level of fluid in the reservoir C so that the syphon will automatically operate once the level of ink in vessel 1 reaches the level of the top of the syphon. The rate of flow of ink through the syphon must exceed the rate of inflow of ink through inlet 2 but can otherwise vary over a wide range. Preferably, the rate of flow of ink through the outlet 5 is from 4 to 50 times that through inlet 2 so that vessel 1 empties in between 2 and 20 seconds.

The vessel 1 is also provided with a vent/overflow pipe 7 to ensure that the headspace in vessel 1 above the ink is at the same pressure as reservoir C both during filling and emptying of vessel 1; and also to provide an emergency overflow in the event that the syphon 6 should fail to operate. Preferably, the back pressure to fluid flow through pipe 7 is substantially less than that through inlet 2 so that little or no back pressure will be exerted on inlet 2 if the syphon fails operate, thus reducing the risk of any back pressure feeding back into the printer ink flow lines and affecting the operation of the print head.

The device of the invention operates automatically without the need for any timer or other controls for valves of pumps to empty vessel 1. The device automatically cycles through the filling and empting cycles at a rate dependent upon the dimensions of the device so that the device can be constructed to give a range of cycle times merely be selecting appropriate inlet and syphon bore sizes. Alternatively, syphon 6 can be provided with a variable restriction thereto, for example a variable setting orifice to outlet 5, so that the rate of flow of ink therethrough can be varied, thus varying the interval between filling cycles. Typically, it will be desired to have an interval of from 1 to 5 minutes between each operating cycle of the device, but the optimum operating cycle times can readily be determined by simple trial and error for any given type of ink jet printer.

In operation, the device of the invention is calibrated using fluids of known viscosities to relate the times taken to fill the vessel 1 between the upper and lower levels to viscosity variations. The device is then installed in an ink jet printer and the viscosity of the ink flowing into the vessel monitored. For a given ink composition, ink feed pressure and printer operating conditions, there will be an acceptable range of viscosity variation corresponding to a range of fillings times for the device. If the device of the invention detects a high filling time outside that range, this will activate a valve on the solvent/carrier supply reservoir E to supply make-up solvent/carrier to the ink circuit, usually to the reservoir C, in an amount corresponding to the extent by which the filling time deviates from the permitted range. Due to the time lag between addition of solvent-/carrier and the diluted ink flowing through the device of the invention, it is preferred to add a number of measured aliquots of solvent/carrier in response to the time variation detected at each cycle of the device of the invention. However, it may be desired to operate the device of the invention at comparatively short intervals and to average out the readings from several cycles before actuating the addition of solvent/carrier medium, thus overcoming the problem of intermittent variations of the composition causing 'hunting' in the ink composition adjustment.

The device and method of the invention provide a simple and effective means for monitoring and adjusting the composition of ink in an ink jet printer without interrupting the operating of the printer and without the need to provide extra control circuitry.

What we claim is:

1. A method for monitoring the viscosity of ink in a continuous jet ink jet printer, which method comprises causing at least part of the ink to flow through a restricted orifice into a vessel and measuring the time taken to fill the vessel between a lower level limit and an upper level limit and allowing ink to escape from the vessel to reduce the level to below the lower level limit, characterised in that ink is automatically removed from the vessel by means of a syphon when the ink has reached at least the said upper level limit.

2. A method as claimed in claim 1 wherein carrier medium or solvent is added to the ink in response to changes in the viscosity monitored so as to maintain the viscosity of the ink within predetermined values.

3. A device for monitoring the viscosity of ink in a continuous ink jet printer which device comprises a vessel having a restricted ink inlet thereto and means for detecting the time taken to fill the vessel between a lower level limit and an upper level limit and an outlet for ink from the vessel, characterised in that the outlet to the vessel is provided with a syphonic means for automatically removing ink from the vessel when ink has reached at least the said upper level limit.

4. A device as claimed in claim 3 further comprising means for controlling the addition of make-up solvent or carrier medium to the ink in response to the viscosity monitored by the device.

5. A device as claimed in claim 3 wherein the distance between the lower and upper level limits is such that it will take from 30 to 300 seconds for the vessel to fill between the level limits.

6. A device as claimed in claim 3 wherein the vessel is provided with an inverted U tube syphon at the outlet thereof which is adapted to empty the vessel automatically once the upper level has been exceeded.

7. A device as claimed in claim 3 wherein the flow of fluid from the vessel through the outlet is from 4 to 50 times the rate of flow of fluid into the vessel via the inlet.

8. A device as claimed in claim 3 wherein sensors are provided to detect the upper and lower level limits, which sensors detect changes in capacitance between the sensor and the wall of the vessel.

9. An ink jet printer which comprises an ink reservoir from which ink is fed under substantially constant pressure via a duct to a print head by a pump to form a series of droplets from a nozzle orifice in the print head, means for selectively directing the line of flight of the droplets onto a substrate on which the droplets are to print an image or into a gutter to catch the droplets and return them to the reservoir, characterized in that a device is connected to said duct for monitoring the viscosity of the ink and in that means are provided for controlling the addition of make-up medium to the ink in response to the viscosity monitored by the device, the device comprising:

a vessel having a restricted ink inlet thereto and means for detecting the time taken to fill the vessel between a lower level limit and an upper level limit and an outlet for ink from the vessel, the outlet from the vessel being provided with a syphonic means for automatically removing ink from the vessel when ink has reached at least the upper level limit.

* * * * *